United States Patent [19]

Kakami et al.

[11] Patent Number: 5,078,711

[45] Date of Patent: Jan. 7, 1992

[54] LASER IRRADIATION DEVICE CAPABLE OF VARYING IRRADIATION ANGLE

[75] Inventors: Kazuhiro Kakami, Gifu; Kenzo Kataoka, Kyoto; Nakajima Tsuneyuki, Kyoto; Hayashida Minoru, Kyoto, all of Japan

[73] Assignee: Kabushiki Kaisha Morita Seisakusho, Kyoto, Japan

[21] Appl. No.: 391,798

[22] Filed: Aug. 9, 1989

[30] Foreign Application Priority Data

Aug. 11, 1988 [JP] Japan .................................. 63-201747
Aug. 8, 1989 [JP] Japan .................................. 1-205454

[51] Int. Cl.$^5$ .............................................. A61N 5/06
[52] U.S. Cl. ...................................... 606/16; 606/15; 128/398
[58] Field of Search ........................ 606/4, 7, 13–18; 128/395, 397, 398, 817

[56] References Cited

U.S. PATENT DOCUMENTS

| | | |
|---|---|---|
| 4,669,467 | 6/1987 | Willett et al. .......................... 606/15 |
| 4,676,231 | 6/1987 | Hisazumi et al. ...................... 606/14 |
| 4,693,244 | 9/1987 | Daikuzono ............................. 606/16 |

Primary Examiner—David Shay
Attorney, Agent, or Firm—Koda and Androlia

[57] ABSTRACT

A laser irradiation device comprising an optical fiber, a contact probe which irradiates laser light from the irradiation end section thereof, and a holding member which coaxially secures the contact probe and the optical fiber. The device is further characterized in that the irradiation angle of the laser light irradiated from the irradiation end section of the contact probe can be changed while the diameter of the contact probe is standardized, whereby the irradiation angle and diffusion conditions of the laser light can be set and changed as desired to improve the transpiration and coagulation capabilities using a low output laser generation unit, thus reducing the coast of.the entire laser irradiation system.

1 Claim, 14 Drawing Sheets

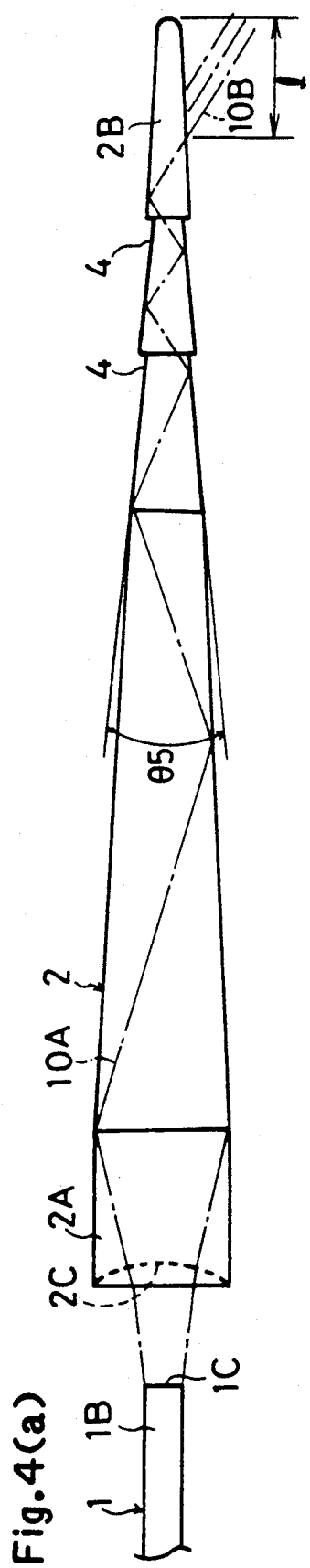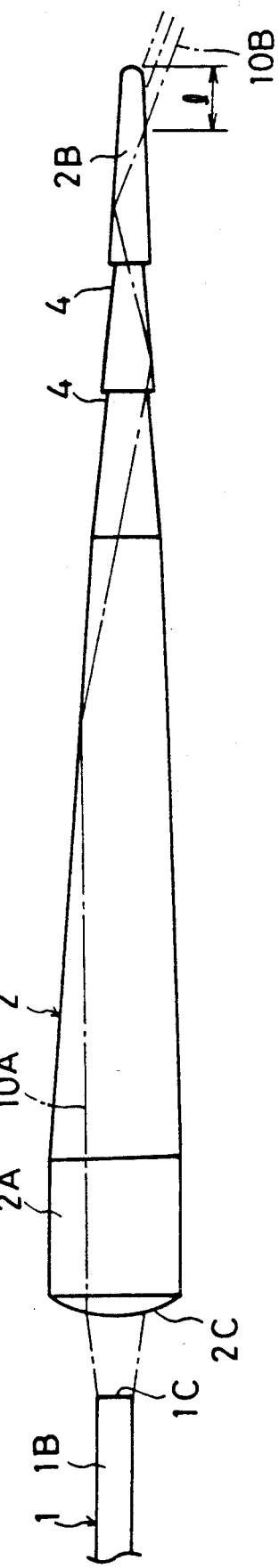

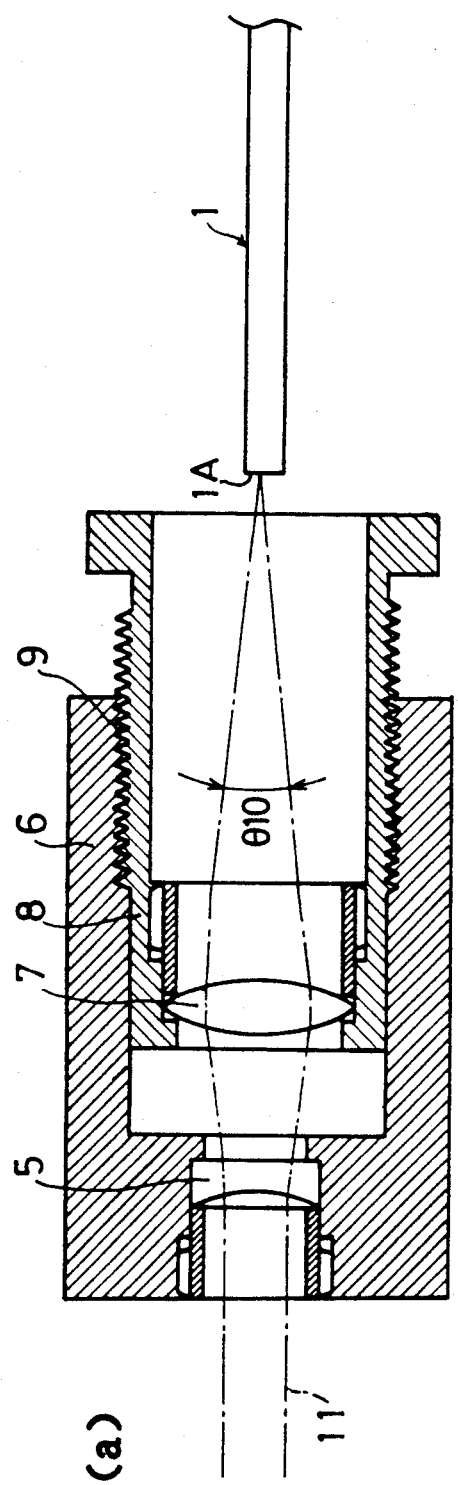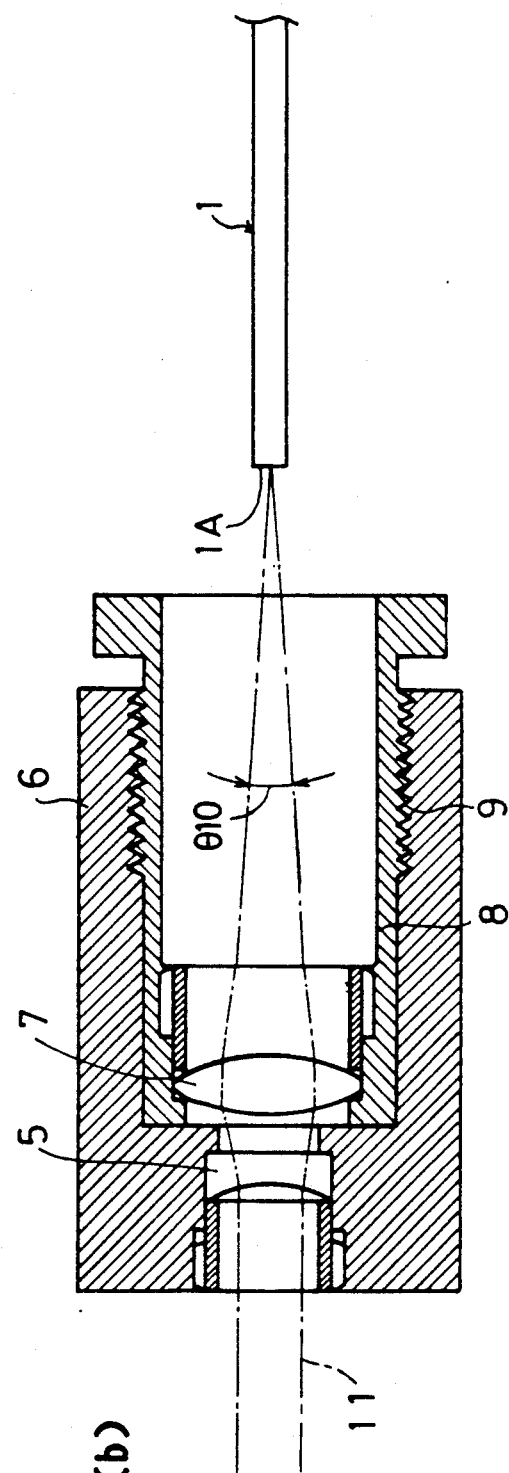
Fig.16(a)
Fig.16(b)

LASER IRRADIATION DEVICE CAPABLE OF VARYING IRRADIATION ANGLE

BACKGROUND OF THE INVENTION

1. Field of the Invention

The present invention relates to a laser irradiation device used for various medical treatments such as transpiration (cutting out) and coagulation (stopping bleeding) of tissues by irradiating intensive laser light to tissues of living bodies, in particular, human bodies.

2. Prior Art

Before describing the prior art of the laser irradiation device for medical treatment, the basic transpiration and coagulation principles by irradiating laser light are described below referring to FIG. 21.

Transpiration and coagulation by laser light irradiation are performed by converting laser light into thermal energy and by applying the energy to tissues. The transpiration and coagulation capabilities greatly depend on the irradiation conditions of the laser light, such as the irradiation angle and diffusion conditions of the laser light.

More specifically, in the case of sharp transpiration which does not require coagulation on the sides of a transpiration section, the laser light 101 should be irradiated in a concentrated beam within a small angle range from the end of a contact probe 100 as shown in FIG. 21 (a).

In the case of fairly deep transpiration which requires coagulation on the sides of a transpiration section, laser light 101 should be irradiated at a large irradiation angle of θ° from the end of the contact probe 100 as shown in FIG. 21 (b). By setting the large irradiation angle θ°, the coagulation capability during transpiration, that is, the capability of stopping bleeding on the sides of the transpiration section is enhanced. In particular, by setting the irradiation angle of the laser light 101 at a uniform value in the range of the irradiation angle θ°, the transpiration on the sides is smoothened and the coagulation capability is enhanced. In addition, the transpiration and coagulation capabilities on the sides are also enhanced. By restricting an excessive output in the axial direction of the probe and distributing the output to the sides, the output of the laser light can be reduced. This can reduce the effect of the laser light to the operator, the patient and the peripheral tissues of the transpiration section. The affected area of the patient can thus less damaged. When a greater transpiration depth is required in the case of transpiration and coagulation at tissues with numerous blood vessels, the laser light 101 should be irradiated from the probe's side having a length from the end to the base section of the contact probe 100 as shown in FIG. 21 (c). The above explanations regarding the relationship between the transpiration and coagulation capabilities and the laser light irradiation angle applies to a contact probe including a cylindrical base section and a tapered cone section being symmetrical around the axis of the probe (hereafter referred to as "a cone probe"). In addition, a hemispheric probe with a hemispheric end which offers a converging convex lens effect and can be pressed against affected areas is primarily used for transpiration. A flat probe with a flat end is primarily used for coagulation at affected areas. Moreover, a point chisel-shaped probe with symmetrical chisel surfaces is primarily used to slantly cut off affected areas. There is no doubt that the transpiration and coagulation capabilities are also greatly dependent on the irradiation and diffusion conditions of the laser light from the end sections of these kinds of various probes in the same way as the above-mentioned cone probe.

A means for changing the incidence energy of the laser light to the incidence end surface at the base section of the probe of a conventional laser irradiation device is generally used to change the transpiration and coagulation capabilities. Other means for changing the capabilities, such as a means for changing the overall length (L1) of the probe 100 with taper angle θ2 to change the irradiation angle θ° of the laser light 101 as shown in FIG. 22 and a means for changing the outside diameter (D2) of the base section of the probe 100 with taper angle θ2 to change the irradiation angle θ° of the laser light 101 as shown in FIG. 23 have been known when cone probes are taken as examples. Among the above-mentioned conventional capability changing means, in the case of the means for changing the incidence energy of the laser light to the incidence end surface at the base section of the probe, the transpiration and coagulation capabilities can be changed by proportionally adjusting the irradiation energy of the laser light depending on the adjustment of the incidence energy of the laser light. However, in that case the transpiration and coagulation capabilities depending on the laser light irradiation angle and diffusion conditions cannot be changed. Accordingly, the increase in rate of the transpiration and coagulation capabilities is low even when the output of the laser generation unit is increased significantly. The increase of the output energy causes danger to the operator and the patient, damage to the tissues of the affected area and early worn-out of the probe. As shown in FIGS. 22 and 23, in the case of the means for changing the overall length of the probe or the diameter of the base section of the probe, the increase rate of the transpiration and coagulation capabilities is restricted depending on clinical purposes, the structural limitations of the holding members used to coaxially secure the probe and the optical fiber, and the operation limitations by the operator.

SUMMARY OF THE INVENTION

Accordingly, it is an object of the present invention to provide a laser irradiation device capable of varying the irradiation angle, which can increase the transpiration and coagulation capabilities using a low output laser generation unit without impairing the operability of the device and can commonly incorporate holding and other members.

Another object of the present invention is to change the irradiation angle at low cost by simply machining a contact probe.

Still another object of the present invention is to improve the transpiration and coagulation capabilities while maintaining the inherent form of the contact probe and securely achieving the intended clinical purposes.

To accomplish the above-mentioned objects, the laser irradiation device capable of varying irradiation angle of the present invention comprises an optical fiber connected to a laser generation unit, a contact probe which irradiates, from the end section of the probe, laser light being incident from the incidence end surface thereof provided facing the irradiation end surface of the end section of the optical fiber, and a holding member which coaxially secures the base section of the contact probe including the incidence end surface thereof and the end section of the optical fiber including the irradiation end surface thereof. The irradiation device is characterized in that the device further comprises a means for changing the irradiation angle of the laser light being irradiated from the end section of the contact probe of the device under the condition that the diameter of the base section of the contact probe is standardized.

The present invention has the following numerous embodiments. With the first embodiment, the irradiation angle changing means comprises a plurality of laser light reflection surfaces which are successively formed on the circumferential surface of the contact probe along the axis thereof and differ in angle to the axis thereof from one another.

With the second embodiment, the irradiation angle changing means comprises a partially tapered step section in which the taper angle of at least one reflection surface is larger than those of the rest of the reflection surfaces.

With the third embodiment, the irradiation angle changing means comprises a combination of a plurality of cylindrical surfaces provided in parallel along the axis of the probe and a plurality of cone surfaces, each diameter of which becomes smaller toward the end of the surface.

With the fourth embodiment, the irradiation angle changing means comprises a plurality of the reflection surfaces formed by the circumferential surfaces with different taper angles on a plurality of contact probes formed coaxially.

With the fifth embodiment, the contact probe is a tapered cone symmetrical around the axis thereof and the irradiation angle changing means comprises partial step sections formed on the circumferential surface of the probe wherein the reflection angle of the incident laser light exceeds the critical angle for reflection of the light and a part of the laser light leaks from the circumferential surface of the probe.

With the sixth embodiment, the irradiation angle changing means comprises a lens-shaped curved surface at the incidence end surface of the contact probe to change the incidence angle.

With the seventh embodiment, the lens-shaped curved surface is concave to increase the incidence angle of the laser light.

With the eighth embodiment, the lens-shaped curve is convex to decrease the incidence angle of the laser light.

With the ninth embodiment, the irradiation angle changing means comprises a combination of a plurality of the reflection surfaces formed on the circumferential surface of the contact probe and having different reflection angles of the laser light and a lens-shaped curved surface on the incidence end surface of the contact probe.

With the tenth embodiment, the irradiation angle changing means incorporates an optical means which can change the irradiation angle of the laser light from the optical fiber and is provided between the irradiation end surface of the end section of the optical fiber and the incidence end surface of the base section of the contact probe, while maintaining the distance between said two surfaces.

With the eleventh embodiment, the irradiation angle changing means incorporates an optical means which can change the irradiation angle of the laser light from the laser generation unit and is provided on the incidence end surface of the base section of the optical fiber, while maintaining the position of the incidence end surface of the base section.

With the twelfth embodiment, the irradiation angle changing means is structured such that the distance between the irradiation end surface of the end section of the optical fiber and the incidence end surface of the base section of the contact probe can be changed.

Other embodiments and their contents will be apparent from the later description of the embodiments wherein the assigned embodiment numbers do not coincide with the above-mentioned manner numbers. Using the present invention having the above-mentioned structures, the laser beam irradiation and diffusion conditions which greatly affect the transpiration and coagulation capabilities can be set and changed as desired by changing the irradiation angle of the laser light irradiated from the end section of the contact probe. Therefore, the transpiration and coagulation capabilities can be increased using a low output laser generation unit, while maintaining the length and diameter of the probe at values suited for easy operation. It is not necessary to extend or expand the length or diameter of the probe to a value larger than that required. In addition, the transpiration and coagulation capabilities can be improved as described above by using the probe, the base section diameter of which is standardized in a certain value. When coaxially securing the end section of the optical fiber and the base section of the probe, the same holding member can be commonly used for any probes having different capabilities. In other words, a single holding member can be interchangeably used with a plurality of probes of different capabilities. Accordingly, by using the present invention, the output of the laser generation unit can be lowered. Because the output of the laser generation unit is proportional to its price, the entire system can be structured at lower cost.

The improvement of the transpiration and coagulation capabilities can be attained at low cost by simple additional machining of the probes of the same specifications while maintaining the probe structure in a shape suited for clinical purposes so that the probes can be used for the various types of the laser light irradiation angle changing means. The means has partially stepped sections with different taper angles along the axis of the circumferential surface of the contact probe, a combination of a cylindrical surface and a tapered surface, a consecutive forming of a plurality of probes along the axis of the contact probe with circumferential surfaces having different taper angles to form a plurality of reflection surfaces with different reflection angles of the laser light, or a lens-shaped (concave or convex) curve at the incidence end surface of the contact probe capable of changing the incidence angle of the laser light.

Furthermore, it is not necessary to machine the probe when an optical means is incorporated as a laser light irradiation angle changing means to change the irradiation angle from the optical fiber, when an optical means is incorporated to change the irradiation angle of the laser light from the laser generation unit or when the distance between the irradiation end surface of the end section of the optical fiber and the incidence end surface of the base section of the probe is changed. Therefore the improvement of the transpiration and coagulation capabilities can be attained while the inherent form of the probe is maintained to achieve the intended clinical purposes.

BRIEF DESCRIPTION OF THE DRAWINGS

FIG. 4 is a side view of the probe of the third embodiment, FIGS. 22 and 23 are side views of the probes incorporating the examples of the conventional capability changing means.

DETAILED DESCRIPTION OF THE INVENTION

First Embodiment

Figure 1:
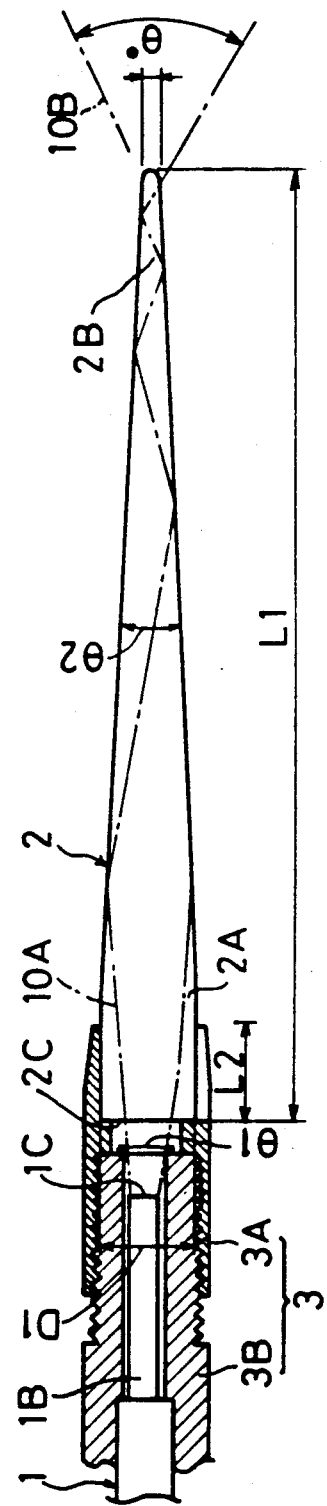
FIG. 1 is a partially cutaway side view illustrating the structure (prior art) of the laser irradiation device related to first, second and third embodiments of the present invention, FIGS. 2 (a), (b) and (c) are side views of the probes of the first embodiment, FIGS. 3 (a) and (b) are side views of the probes of the second embodiment.

This embodiment applies to a laser irradiation device equipped with a cone probe. As shown in FIG. 1, the embodiment comprises an optical fiber 1 which is connected to a laser generation unit (not shown) and optically converges parallel laser light generated from the laser generation unit at a certain angle then conducts the laser light, a cone contact probe 2 which reflects laser light 10A being incident at the maximum diverging angle from the incidence end surface 2C provided facing the irradiation end surface 1C of the optical fiber 1, and a holding member 3 composed of a pair of cylindrical male and female screw members 3A and 3B screw-connectable to each other so that the cylindrical base section 2A including the incidence end surface 2C of the probe 2 is coaxially secured with the end section 1B including the irradiation end surface 1C of the optical fiber 1.

Figure 2A:
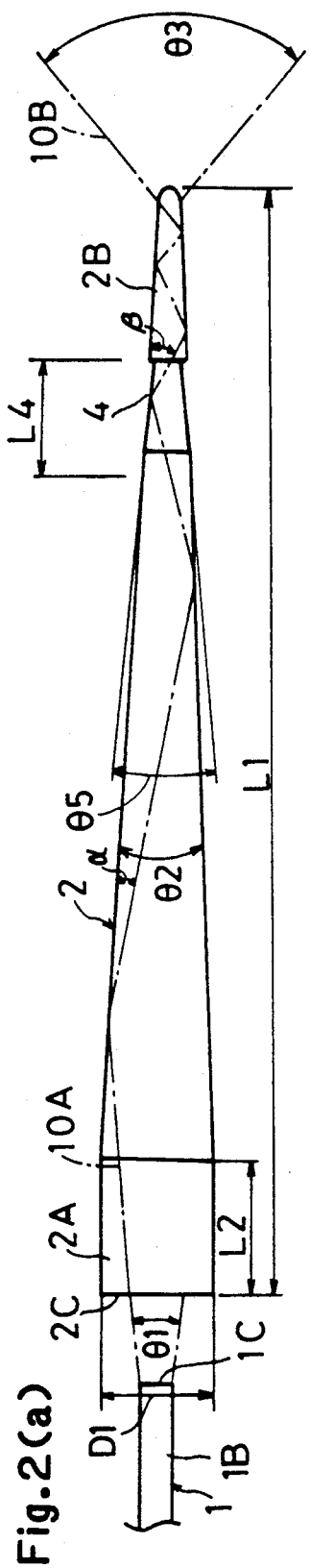
Figure 2B:
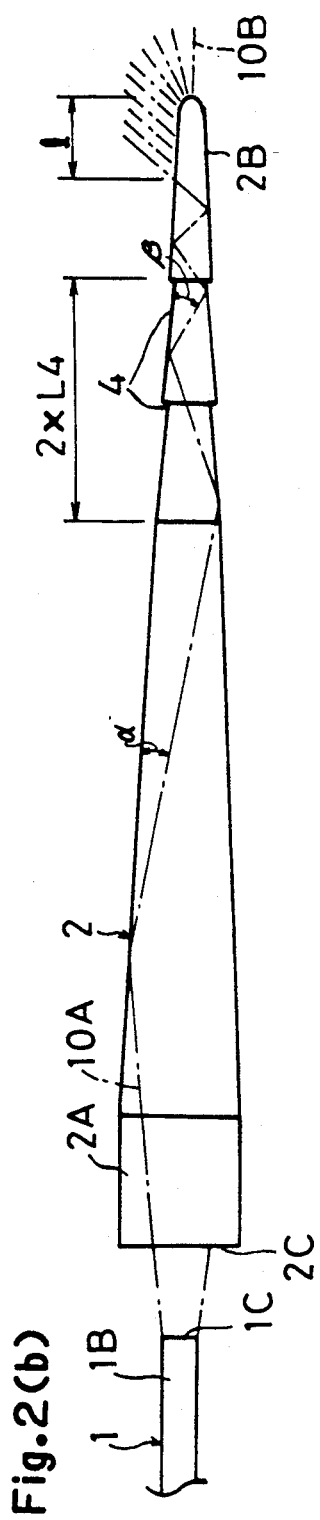
Figure 2C:
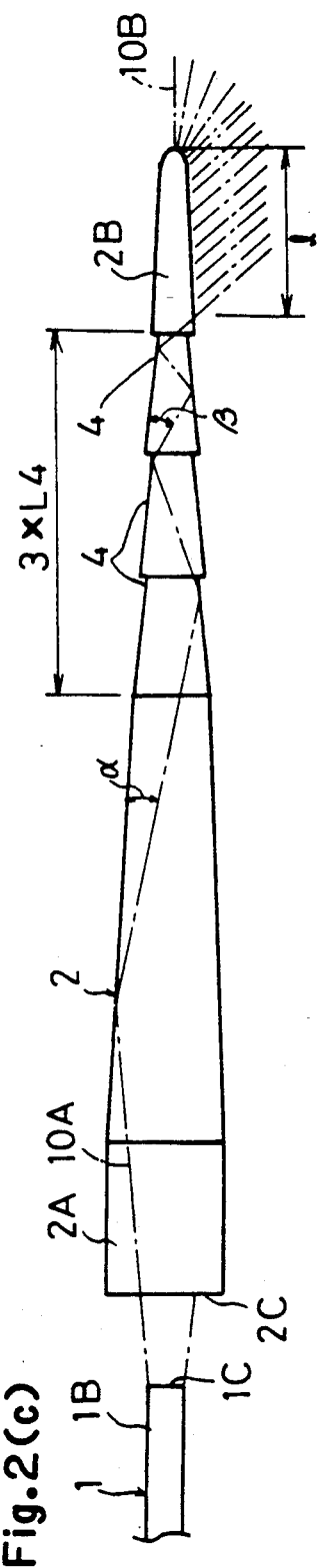

With this embodiment, a laser light irradiation angle changing means shown in FIG. 2 has been added to the laser irradiation device having the above-mentioned structure (prior art). Referring to FIG. 2, the overall length (L1) of the probe 2, the length (L2) of the cylindrical base section 2A, the incidence angle ($\theta 1$) to the incidence end surface 2C, the taper angle ($\theta 2$) of the probe 2 and the outside diameter (D1) of the cylindrical base section 2A are standardized. On the circumferential surface of the probe 2 between the base section 2A and the end section 2B, a partially tapered step section 4 with a length (L4) and a taper angle ($\theta 5$) being larger than the taper angle ($\theta 2$) of the probe 2 is formed to function as the above-mentioned irradiation angle changing means. The taper angle ($\theta 5$), the length (L4) and the number of the partially tapered step sections 4 have been determined by considering the relationship to the values of the lengths (L1 and L2), the angles ($\theta 1$ and $\theta 2$) and the diameter (D2) so that the laser light 10A can be irradiated from the end section 2B in the desired pattern. FIG. 2 (a) shows a device with one tapered step section 4, FIG. 2 (b) shows a device with two tapered step sections 4 and FIG. 2 (c) shows a device with three tapered step sections 4. In the case of the device shown in FIG. 2 (a), the laser light 10B has a large irradiation angle ($\theta 3$) to improve the transpiration and coagulation capabilities. In the cases of the devices shown in FIGS. 2 (b) and (c), the laser light 10B is irradiated from the side surface with a certain length (1) on the end section 2B to improve the transpiration and coagulation capabilities at tissues including many veins.

In the first embodiment, the irradiation angle ($\theta 3$) of the laser light 10B and the irradiation range length (1) on the side can be set as desired by changing the number of steps, the length (L4), the taper angle ($\theta 5$) of the partially tapered step section 4 and the positions and space of a plurality of the partially tapered step sections 4.

Instead of the cylindrical base section, a single cone shape along the entire length of the probe can be used in the case of the first embodiment.

Second embodiment

This embodiment applies to the laser irradiation device equipped with a cone probe, which is basically identical to the first embodiment. The overall length (L1) of the probe 2, the length (L2) of the cylindrical base section 2A, the incidence angle ($\theta 1$) to the incidence end surface 2C, the taper angle ($\theta 2$) of the probe 2 and the outside diameter (D1) of the cylindrical base section 2A are standardized. The incidence end surface 2C of the probe 2 has a curved surface of a concave lens as shown in FIG. 3 (a) or has a curved surface of a convex lens as shown in FIG. 3 (b).

Figure 3A:
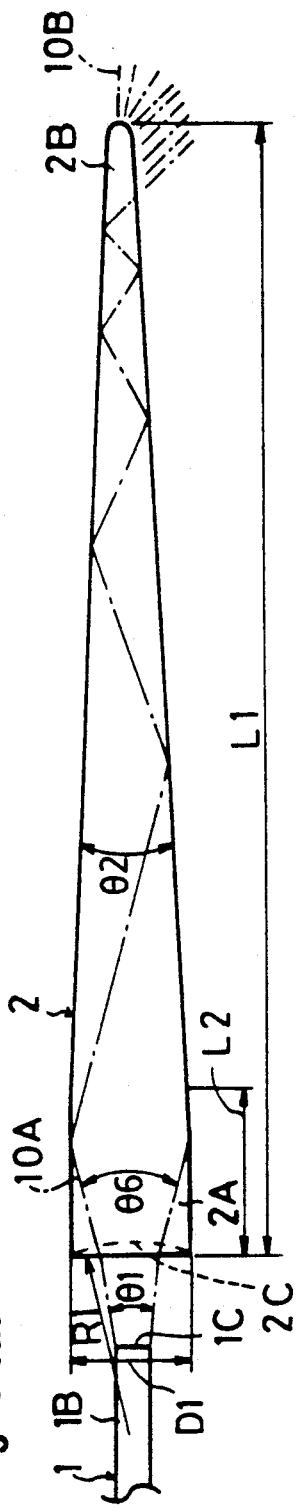
Figure 3B:
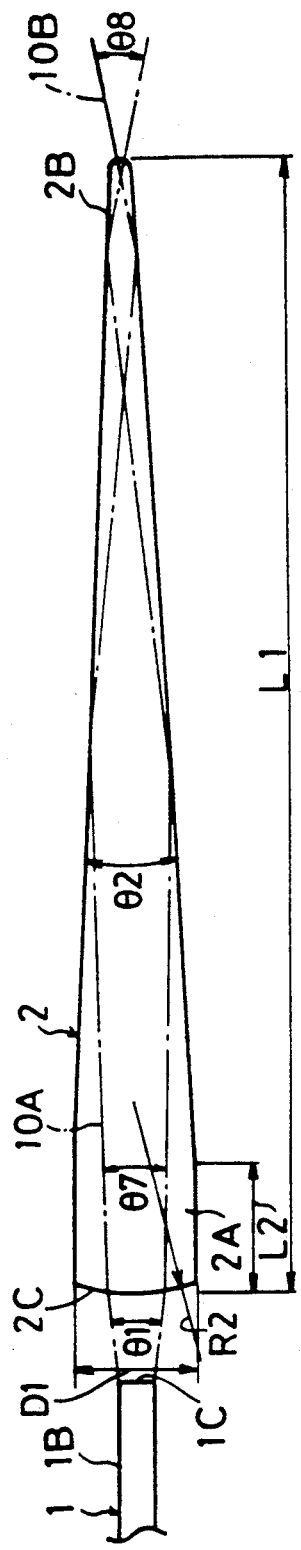

In the case of the device shown in FIG. 3 (a), the incidence angle ($\theta 6$) is larger than the incidence angle ($\theta 1$) at the incidence end surface 2C. The coagulation capability can be improved by irradiating the laser light 10B from the side of the end section 2B. In the case of the device shown in FIG. 3 (b), the incidence angle ($\theta 7$) is smaller than the incidence angle ($\theta 1$). The irradiation angle ($\theta 8$) of the laser light 10B at the end section 2B is small and thus sharp transpiration is possible. With the second embodiment, the laser light irradiation length and angle from the side surface of the probe can be set as desired by changing the curvature radius (R1) of the concave lens-shaped curvature surface, 2C and the curvature radius (R2) of the convex lens-shaped curvature surface 2C.

Third Embodiment

This embodiment applies to the laser irradiation device equipped with a cone probe. The structure and the specifications (L1, L2, $\theta 1$, $\theta 2$ and D1) are the same as those of the first and second embodiments. The partially tapered step section 4 with a taper angle ($\theta 5$) is formed at the circumferential surface close to the end section 2B of the probe 2. The incidence end surface 2C of the probe 2 has a curved surface of a concave lens as shown in FIG. 4 (a) or has a curved surface of a convex lens as shown in FIG. 4 (b). With the combination, the irradiation angle and diffusion conditions for the laser light 10B irradiated from the end section 2B of the probe 2 can be changed so that the transpiration and coagulation capabilities can be changed as desired. The number of the tapered step sections 4 of the third embodiment can be two as shown in FIGS. 4 (a) and (b) or one or three or more.

Fourth Embodiment

Figure 5:
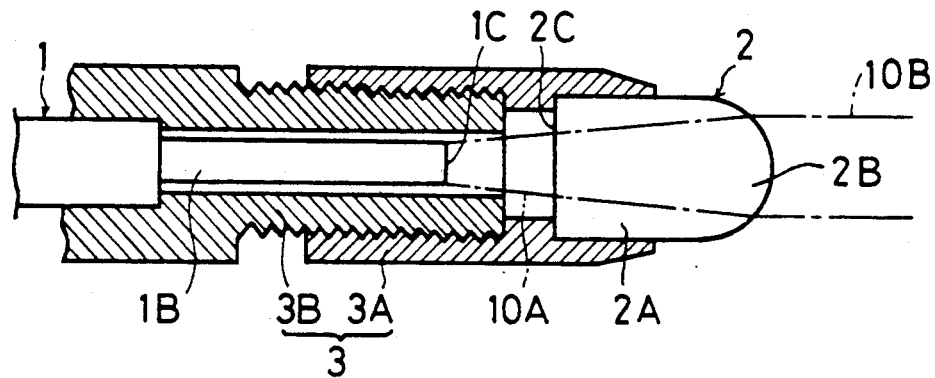
FIG. 5 is a partially cutaway side view illustrating a prior art structure of a laser irradiation device upon which to a fourth embodiment of the present invention is based, FIG. 6 (a) and (b) are side views of the probes of the fourth embodiment.

This embodiment applies to the laser irradiation device equipped with a hemispherical probe mainly used for transpiration. The mechanical details of the coupling between the fiber optic and the probe of the fourth embodiment are as shown in FIG. 5. In particular, the embodiment has a structure comprising an optical fiber 1 which is connected to a laser generation unit (not shown) and conducts laser light from the laser generation unit, a hemispherical probe 2 which converges the laser light 10A being incident from the incidence end surface 2C provided facing the irradiation end surface 1C of the optical fiber 1 using the convex lens's converging effect and irradiates the laser light 10B from the hemispherical end section 2B which can be pressed against the affected area of the patient, and a pair of cylindrical male and female screw members 3A and 3B screw-connectable to each other so that a cylindrical base section 2A including the incidence end surface 2C of the probe 2 is coaxially secured with the end section 1B including the irradiation end surface 1C of the optical fiber 1.

Figure 6A:
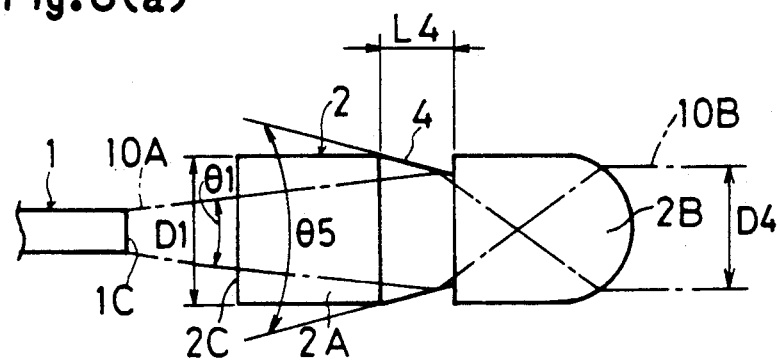
Figure 6B:
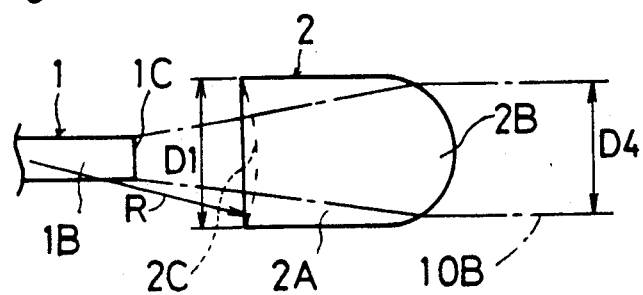

With the laser irradiation device having the above-mentioned structure, the outside diameter (D1) of the cylindrical base section 2A of the probe 2 and the incidence angle ($\theta 1$) to the incidence end surface 2C are standardized. On the circumferential surface of the probe 2, the partially tapered step section 4 with a length (L4) and a taper angle ($\theta 5$) is formed as shown in FIG. 6 (a). The incidence end surface 2C of the probe 2 is formed on the concave (or convex) lens-shaped curved surface with a curvature radius (R) as shown in FIG. 6 (b). The irradiation diameter (D4) of the laser light 10B from the end section 2B can be set as desired using the tapered step section or curvature section.

Fifth embodiment

Figure 7:
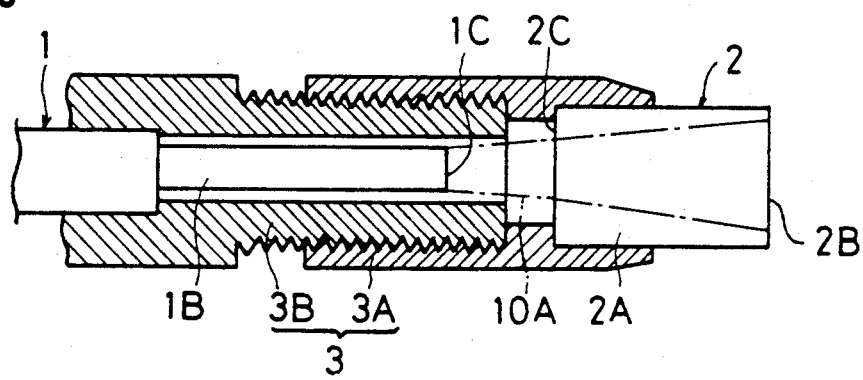
FIG. 7 is a partially cutaway side view illustrating the structure of the laser irradiation device related to a fifth embodiment of the present invention, FIGS. 8 (a) and (b) are side views of the probes of the fifth embodiment.
Figure 8A:
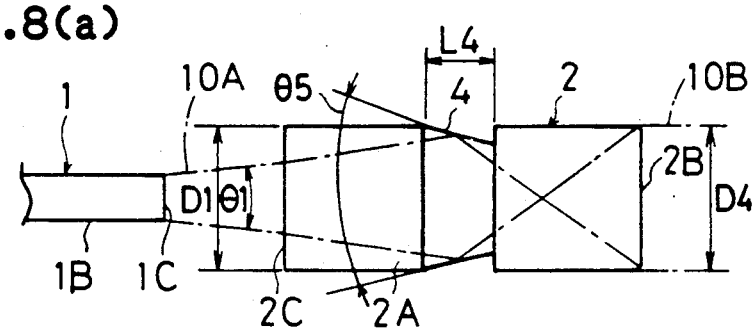
Figure 8B:
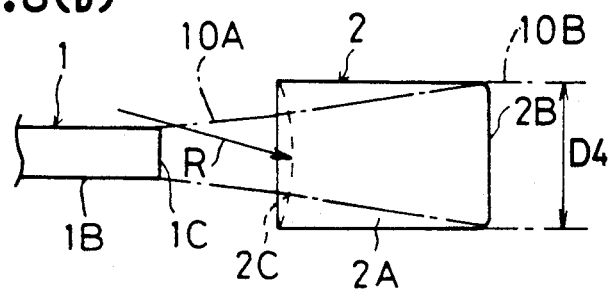

This embodiment applies to the laser irradiation device equipped with a flat probe mainly used for coagulation. As shown in FIG. 7, the embodiment comprises an optical fiber 1, a flat probe 2 comprises a flat end section 2B and a holding member including a pair of cylindrical male and female screw members 3A and 3B screw-connectable to each other in the same way as the fourth embodiment. With the laser irradiation device having the above-mentioned structure, the outside diameter (D1) of the cylindrical base section 2A of the probe 2 and the incidence angle ($\theta 1$) to the incidence end surface 2C are standardized. On the circumferential surface of the probe 2, the partially tapered step section 4 with a length (L4) and a taper angle ($\theta 5$) are formed as shown in FIG. 8 (a). The incidence end surface 2C of the probe 2 is formed on the concave (or convex) lens-shaped curved surface with a curvature radius (R) as shown in FIG. 8 (b). The irradiation diameter (D4) of the laser light 10B can be set as desired using the tapered step section or curvature section in the same way as the fourth embodiment.

Sixth Embodiment

Figure 9:
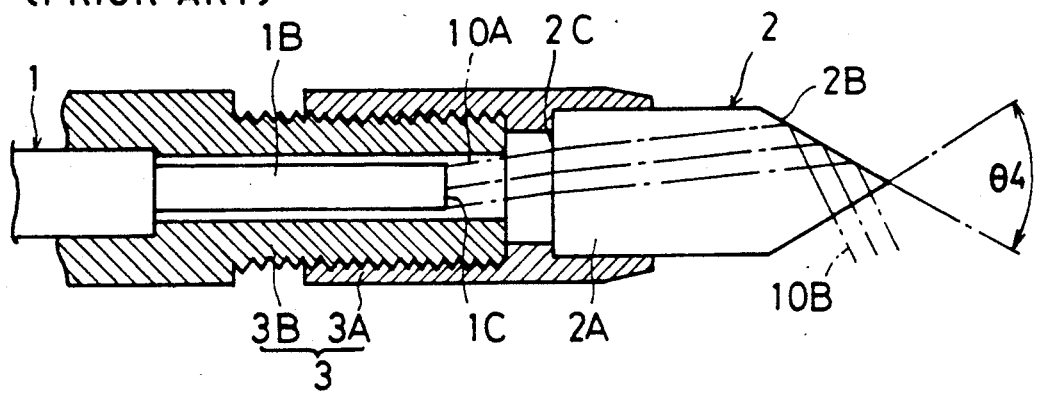
FIG. 9 is a partially cutaway side view illustrating a prior art structure of a laser irradiation device upon which a sixth embodiment of the present invention is based, FIGS. 10 (a) and (b) are side views of the probes of the sixth embodiment.
Figure 10A:
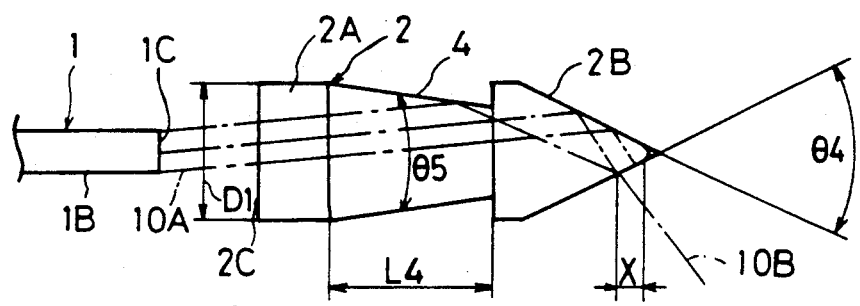
Figure 10B:
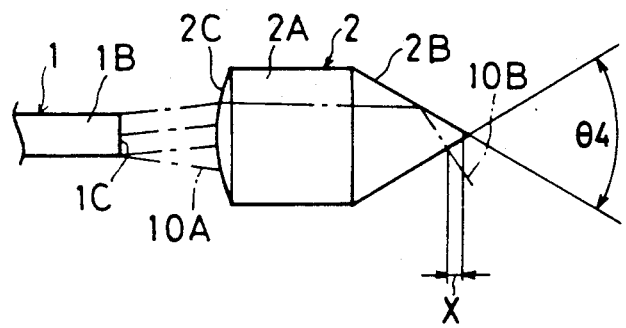

This embodiment applies to the laser irradiation device equipped with a point chisel-shaped probe mainly used for slantly cutting off affected areas. The mechanical details of the coupling between the fiber optic and the probe of the sixth embodiment are as shown in FIG. 9. In particular, the embodiment comprises an optical fiber 1, a point chisel-shaped probe 2 including an end section 2B with symmetrical chisel surfaces and an edge right-angled to the axis of the probe, and a holding member 3 composed of a pair of cylindrical male and female screw members 3A and 3B in the same way as the fourth and fifth embodiments. The irradiation length (X) of the end section 2B of this type should be as short as possible. The taper angle ($\theta 4$) of the end section 2B, the outside diameter (D1) of the cylindrical base section 2A and the incidence angle ($\theta 1$) to the incidence end surface 2C are standardized. On the circumferential surface of the probe 2, the partially tapered step section 4 with a length (L4) and a taper angle ($\theta 5$) are formed as shown in FIG. 10 (a). The incidence end surface 2C of the probe 2 is formed on the convex lens-shaped or cylindrical curvature surface. With this type, the irradiation length (X) of the end section 2B can be set as desired.

Seventh Embodiment

Figure 11:
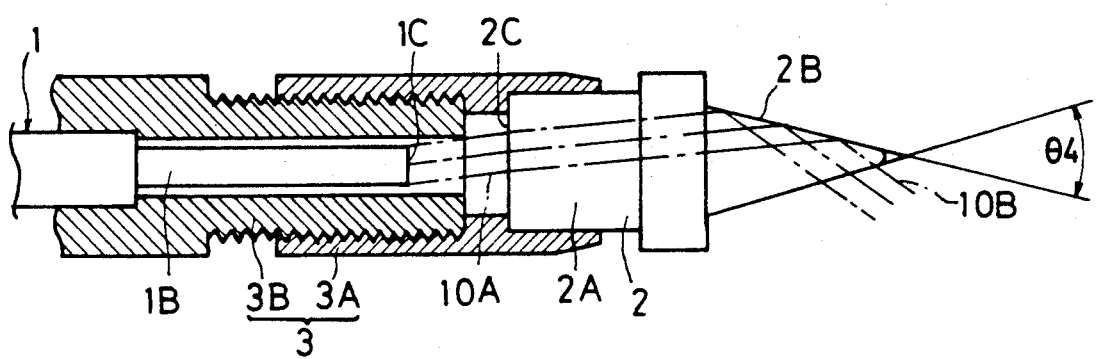
FIG. 11 is a partially cutaway side view illustrating a prior art structure of a laser irradiation device upon which to a seventh embodiment of the present invention is based, FIG. 12 (a) and (b) are side views of the probe of the seventh embodiment, FIGS. 13 (a) to (i) are side views of the probes of an eighth embodiment, FIG. 13 (j) is a sectional view taken on line X—X of FIG. 13 (i), FIG. 14 (a) to (d) are side views of the probes of a ninth embodiment, FIGS. 15 (a) and (b) are vertical sectional side views of major sections of a tenth embodiment, FIG. 16 (a) and (b) are enlarged vertical sectional side views of the laser irradiation device related to an eleventh embodiment, FIGS. 17 (a) and (b) are enlarged vertical sectional side views of major sections of the laser irradiation device related to a twelfth embodiment.
Figure 12A:
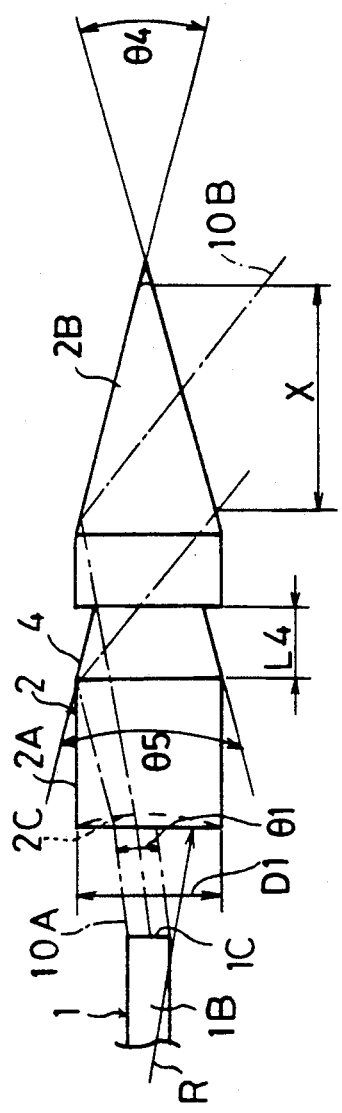
Figure 12B:
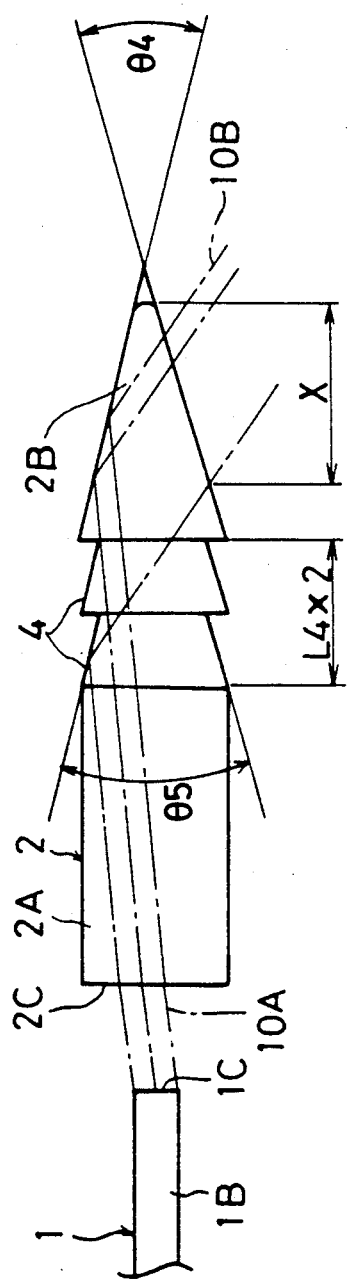
Figure 13A:
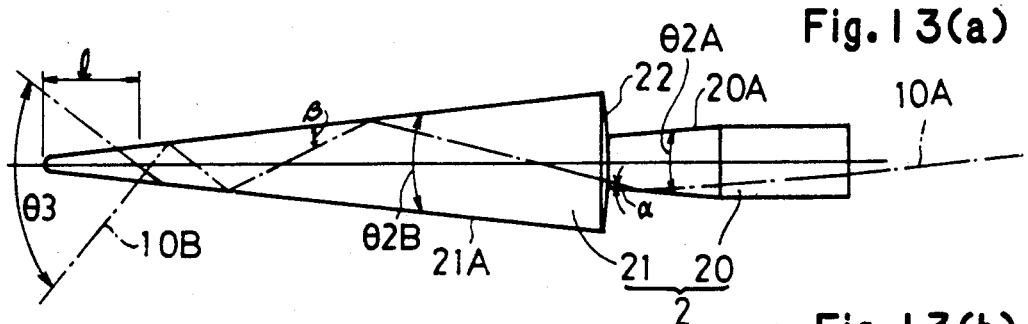
Figure 13B:
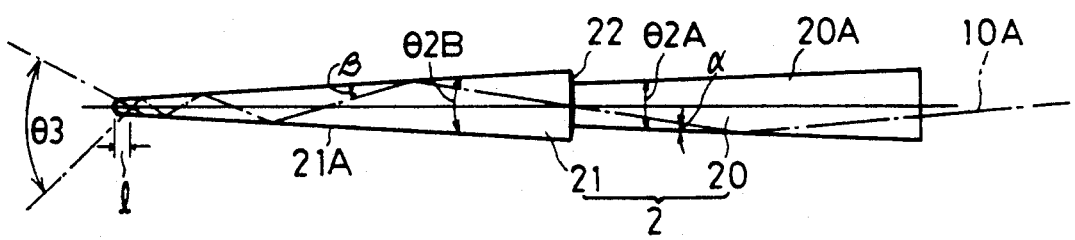
Figure 13C:
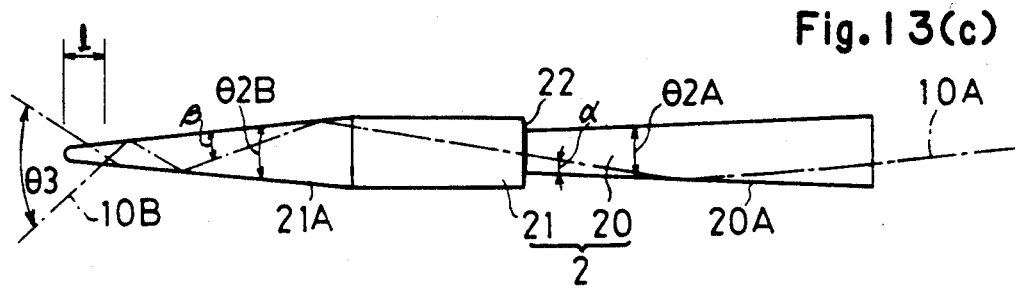
Figure 13D:
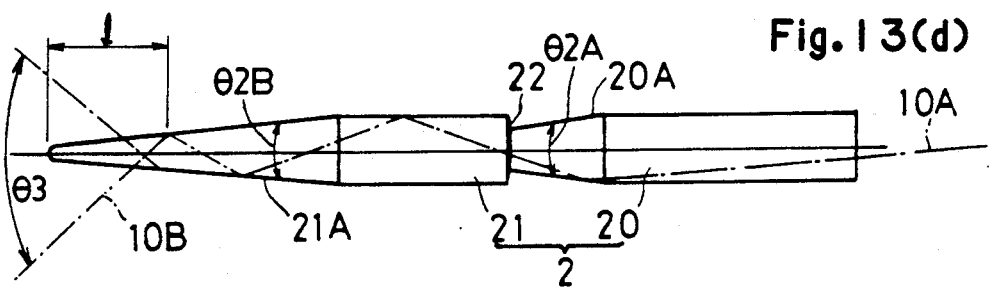
Figure 13E:
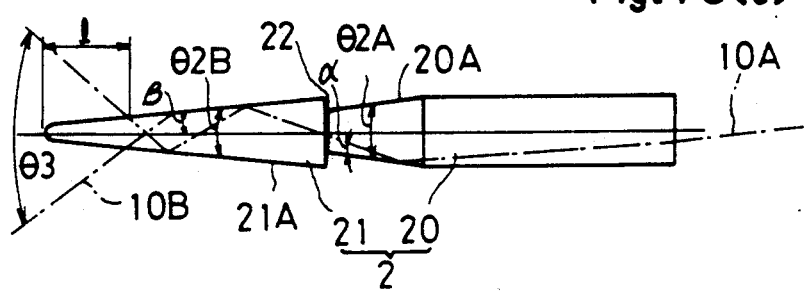
Figure 14A:
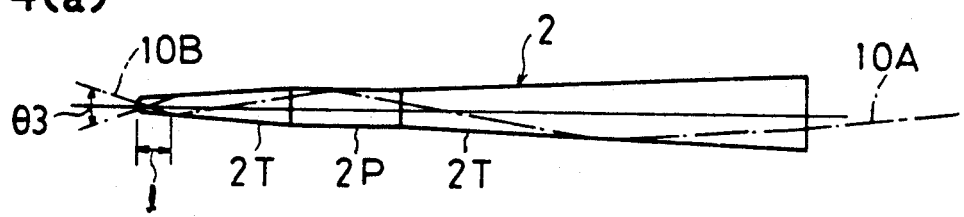
Figure 14B:
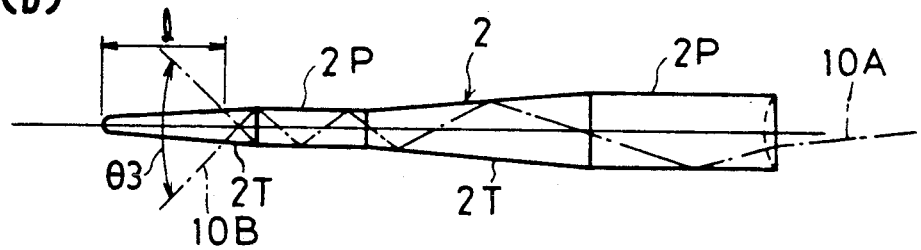
Figure 14C:
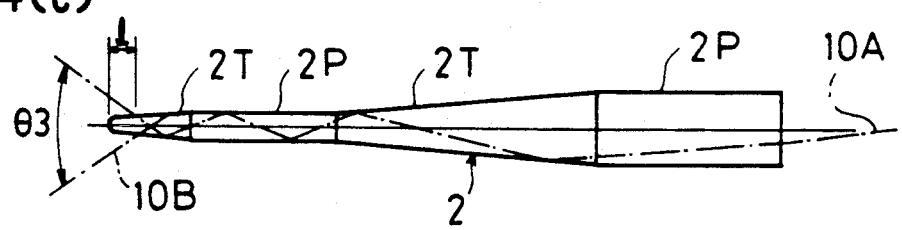
Figure 14D:
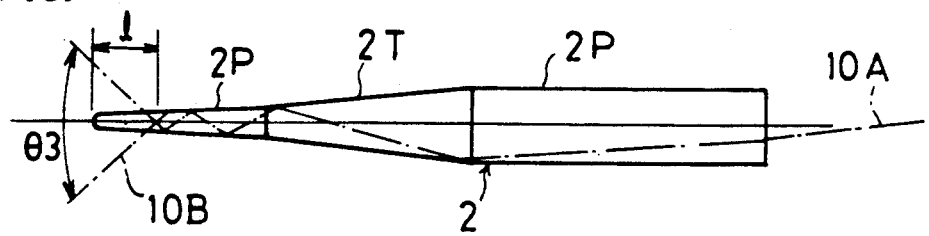

This embodiment applies to a laser irradiation device equipped with a short probe used for high-speed transpiration and uniform heating of affected areas. The mechanical details of the coupling between the fiber optic and the probe of the seventh embodiment are as shown in FIG. 11. In particular, the embodiment comprises an optical fiber 1, a short cone probe 2 having a cone end section 2B and irradiates the laser light 10B from the entire surface of the taper section, and a holding member 3 composed of a pair of cylindrical male and female screw members 3A and 3B in the same way as the above-mentioned embodiments. With this type, the laser light 10B should be irradiated from the entire surface of the end section 2B. The taper angle ($\theta 4$) of the end section 2B, the outside diameter (D1) of the cylindrical base section 2A and the incidence angle ($\theta 1$) to the incidence end surface 2C are standardized. On the circumferential surface of the probe 2, a partially tapered step section 4 with a length (L4) and a taper angle (θ5) is formed and the incidence end surface 2C of the probe 2 is formed on the concave lens-shaped curved surface with a curvature radius (R) as shown in FIG. 12 (a). Or two partially tapered step sections 4 with a length (L4) and a taper angle (θ5) are formed as shown in FIG. 12 (b). With these types, the irradiation length (X) of the tapered end section 2B can be changed as desired.

Eighth Embodiment

In a laser irradiation device equipped with a cone probe used in the above-mentioned first, second and third embodiments, the device of this embodiment is another example of the means for forming a plurality of reflection surfaces with different reflection angles of the laser light. The devices shown in FIGS. 13 (a) to (f) have two probe members 20 and 21 with circumferential surfaces 20A and 21A having different taper angles (θ2A) and (θ2B). The two probe sections are consecutively formed along the same axis to form a single probe 2. Around the tapered surfaces 20A and 21A of the probe sections 20 and 21, a plurality of reflection surfaces with different reflection angles (α) and (β) of the laser light 10A are formed. In addition, a circular step section 22 is projected outward perpendicular to the axis of the probe at the border section of the probe sections 20 and 21. The device shown in FIG. 13 (g) is a formation of a probe section 20 with a cylindrical surface 20B which extends to its entire length along the axis of the probe 2 and a probe section 21 with a circumferential surface 21A with a constant taper angle (θ2B) to form a single probe 2. A circular step section 22 similar to the one described above is formed at the border section of the probe sections 20 and 21. The device shown in FIGS. 13 (h) and (i) comprises three probe sections 20, 21 and 21' with circumferential surfaces 20A, 20B and 20C having different taper angles (θ2A),(θ2B) and (θ2C) along the same axis to form a single probe 2. In particular, the device shown in FIG. 13 (h) comprises a plurality of micro-step sections 23 composed of V-shaped circular grooves around the end section of the probe section 21' located closest to the end section. The device shown in FIG. 13 (i) has a plurality of grooves 24 shown in FIG. 13 (j) along the axis around the end section of the probe section 21' located closest to the end section to change the laser light irradiation condition at the end section. In the case of the embodiments shown in FIGS. 13 (a) to (i), by forming a plurality of probe sections, a laser irradiation device with a desired irradiation angle (θ3) and a desired side irradiation range (l) can be made. This type can be produced by either of cutting a single spindle or joining separate probe

Ninth Embodiment

In a laser irradiation device equipped with a cone probe used in the above-mentioned first, second and third embodiments, the device of this embodiment is still another example of the means for forming a plurality of reflection surfaces with different reflection angles of the laser light. As shown in FIGS. 14 (a) to (d), on the circumferential surface of the probe 2, one or a plurality of cylindrical surfaces 2P along the axis of the probe 2 are formed with one or a plurality of tapered surfaces 2T, the diameter of which is smaller at a point closer to the end section, by setting the irradiation angle (θ3) of the laser light from the end section of the probe and the irradiation range (l) at the side surface as desired.

This type can be produced in the same way as that of the eighth embodiment.

Tenth Embodiment

Figure 15A:
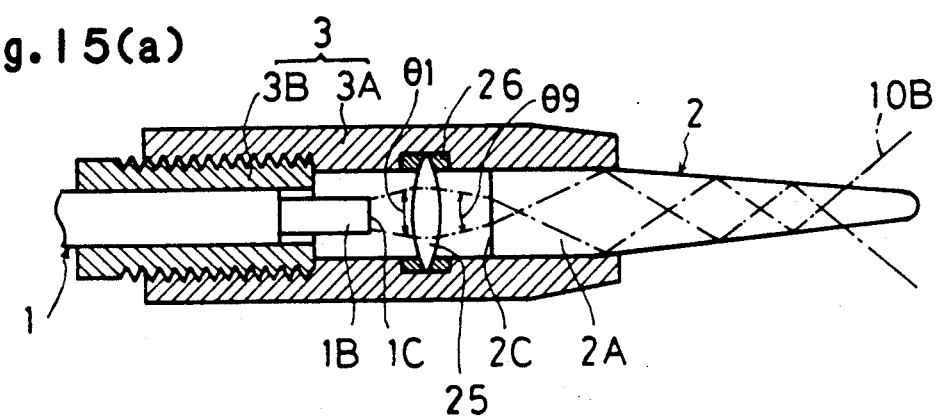
Figure 15B:
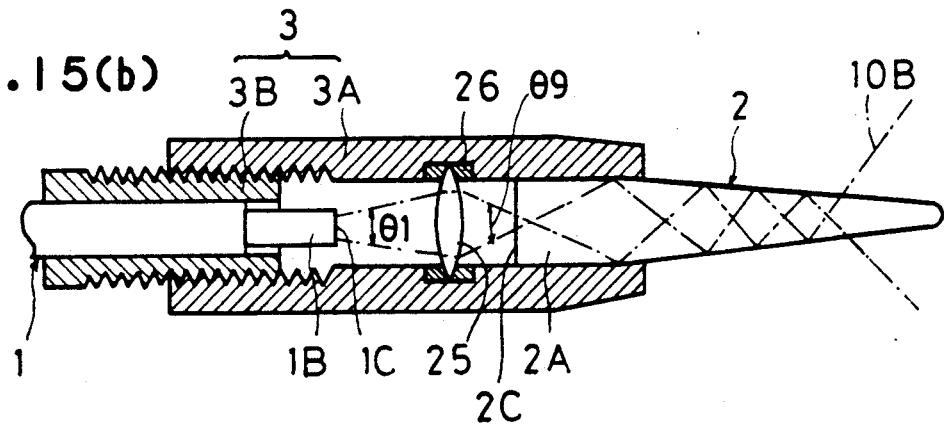

As shown in FIGS. 15 (a) and (b), an optical lens capable of changing the irradiation angle (θ1) of the laser light from the optical fiber 1 is incorporated between the irradiation end surface 1C at the end section of the optical fiber 1 and the incidence end surface 2C of the base section 2A of the contact probe 2 to change the irradiation angle of the laser light from the end section of the contact probe 2. More specifically, a pair of male and female screw members 3A and 3B are used to coaxially secure the end section 1B including the irradiation end surface 1C of the optical fiber 1 with the base section 2A of the probe 2, and a convex lens 25 is secured via a holding member 26 on the cylindrical screw member 3A. By relatively moving the screw members 3A and 3B along the optical axis, the distance between the irradiation end surface 1C of the fiber 1 and the convex lens 25 is changed. This changes the incidence angle (θ9) at the probe 2.

Eleventh Embodiment

As shown in FIGS. 16 (a) and (b), with the incidence end surface 1A of the base section of the optical fiber 1 set at a constant position, an optical means capable of changing the converging angle (θ7) of the parallel laser light 11 from a laser generation unit (not shown) is incorporated to change the irradiation angle of the laser light irradiated from the end section of the contact probe 2. More specifically, a cylindrical member 6 equipped with a fixed lens 5 on which the laser light 11 is incident is provided on the side of the incidence end surface 1A of the optical fiber 1. A movable cylindrical member 8 equipped with a convex lens 7 which is coaxial to the fixed lens 5 is coaxially fit in the cylindrical member 6 so that the movable member 8 can be moved along the optical axis and fixed via a screw section 9.

Twelfth Embodiment

Figure 17A:
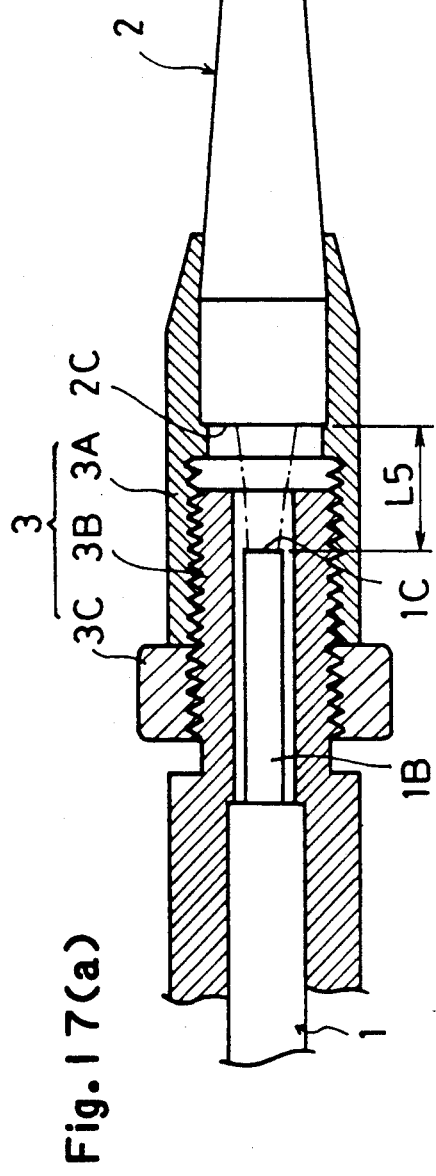
Figure 17B:
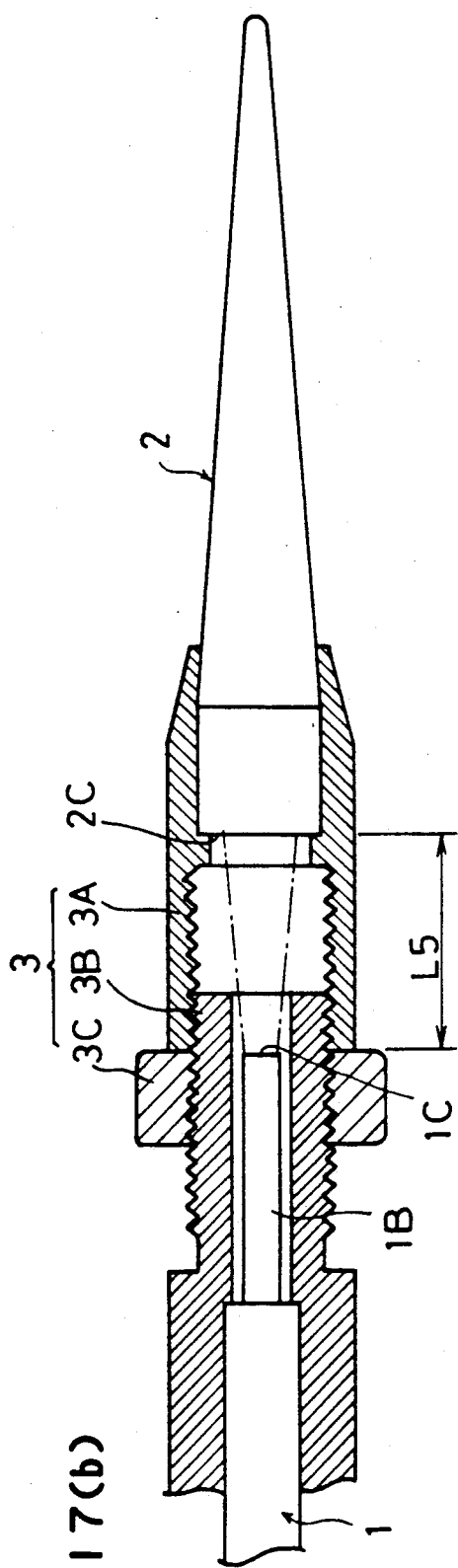

As shown in FIGS. 17 (a) and (b), the distance (L5) between the irradiation end surface 1C of the optical fiber 1 and the incidence end surface 2C of the contact probe 2 is changed to change the diameter of the laser light in the probe 2. By changing the diameter, the irradiation angle of the laser light from the end section 2B of the contact probe 2 can be changed. More specifically, a pair of male and female cylindrical screw members 3A and 3B of the holding member 3 for coaxially securing the optical fiber 1 and the probe 2 are movable along the optical axis and can be fixed via a lock nut 3C at the desired distance (L5).

Various types are obtained without changing the specifications of the probe 2. In addition, the irradiation angle and diffusion conditions can be changed without replacing the probe 2.

Other Embodiments

Figures 18, 19, 20:
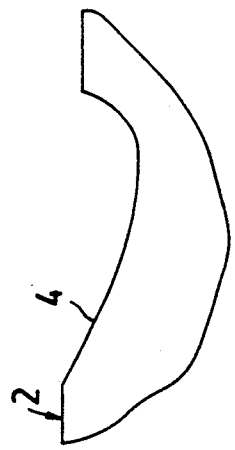
FIGS. 18 to 20 are enlarged side views illustrating modification examples of partially tapered step sections, FIGS. 21 (a) to (c) are side views illustrating the relationship between the transpiration and coagulation capabilities and laser light irradiation angles.
Figure 21A:
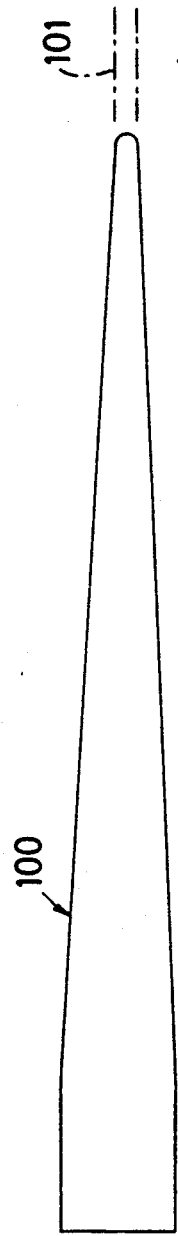
Figure 21B:
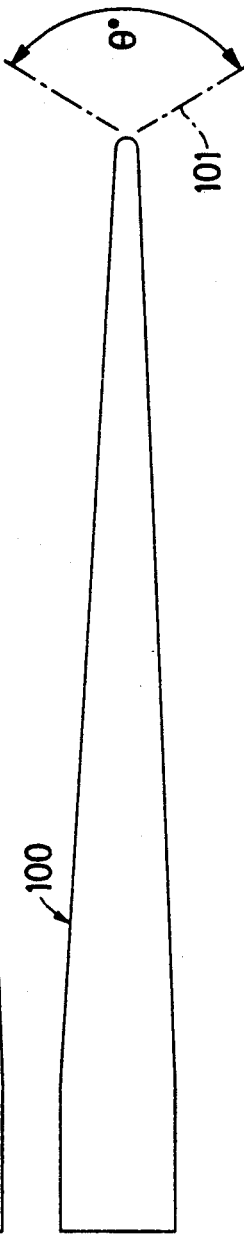
Figure 21C:
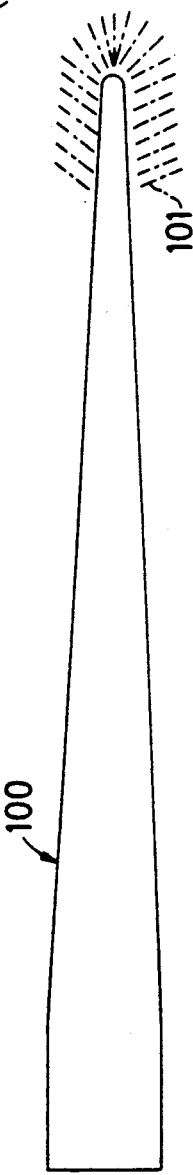

The partially tapered step sections 4 shown in the above-mentioned embodiments can have a V-shaped form shown in FIG. 18. Alternately, the partial step section can also be formed by a concaved circular arc surface as a reflection surface shown in FIG. 19 and a concaved complex curve surface shown in FIG. 20. The holding member 3 can have various structures other than those shown in the above-mentioned embodiments.

We claim:

1. A laser irradiation device capable of varying an irradiation angle comprising an optical fiber connected at one end to a laser generation unit, a probe connected to another end of said optical fiber which irradiates, from an irradiation end section of said probe, laser light being incident from an incidence end surfaced thereof provided facing an irradiation end surface of an end section of said optical fiber, and a holding member which coaxially secures a base section of said probe including the incidence end surface thereof and said end section of said optical fiber including the irradiation end surface thereof, said device further comprising a means for changing the irradiation angle of said laser light being irradiated from said irradiation end section of said probe of said device while the diameter of said base section of said probe is standardized, and wherein said probe has a light transmitting tapered cone section being symmetrical around an axis thereof;

said irradiation angle changing means comprises a plurality of laser light reflection surfaces which are successively formed on a circumferential surface of said probe along said axis thereof and differ in angle to said axis thereof from one another;

at least one of said plurality of reflection surfaces includes a partial step section, the angle to said axis of which is larger than those of remaining said reflection surfaces;

said probe comprises a plurality of probe sections with different tapered angles formed consecutively along said axis of said probe and said plurality of reflection surfaces are formed by circumferential surfaces of said probe sections; and said irradiation angle changing means comprises said reflection surfaces formed on said circumferential surface of said probe so that the reflection angle of said incident laser light to said probe exceeds a critical angle for reflection of said light and a part of said lacer light leaks from said circumferential surface of said probe.

* * * * *